United States Patent
Kim et al.

(10) Patent No.: US 11,278,365 B2
(45) Date of Patent: Mar. 22, 2022

(54) ARTICULATING STRUCTURE USING ROLLING JOINT AND PROJECTION MEMBER, AND TUBE INSERT DEVICE HAVING THE SAME

(71) Applicant: KOREA INSTITUTE OF SCIENCE AND TECHNOLOGY, Seoul (KR)

(72) Inventors: Keri Kim, Seoul (KR); Seong Il Kwon, Seoul (KR); Jeongryul Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 129 days.

(21) Appl. No.: 16/711,434

(22) Filed: Dec. 12, 2019

(65) Prior Publication Data
US 2020/0360101 A1    Nov. 19, 2020

(30) Foreign Application Priority Data
May 15, 2019    (KR) .................... 10-2019-0056877

(51) Int. Cl.
*A61B 34/00* (2016.01)
(52) U.S. Cl.
CPC .................... *A61B 34/71* (2016.02)
(58) Field of Classification Search
CPC .............. A61B 1/008; A61B 34/71; A61B 2017/00323; B25J 9/106; B25J 9/065; B25J 17/025
See application file for complete search history.

(56) References Cited

U.S. PATENT DOCUMENTS 1,314,601 A * 9/1919 McCaskey .............. F16D 3/04
                                                464/147
3,583,393 A * 6/1971 Takahashi ............ A61B 1/0055
                                                600/142
(Continued)

FOREIGN PATENT DOCUMENTS

JP    2016528946 A    9/2016
KR    101280065 B1    6/2013
(Continued)

OTHER PUBLICATIONS

Yong-Jae Kim et al. "A Stiffness-Adjustable Hyperredundant Manipulator Using a Variable Neutral-Line Mechanism for Minimally Invasive Surgery," IEEE Transactions on Robotics, Apr. 2014, pp. 382-395, vol. 30, No. 2.

*Primary Examiner* — Bobby Rushing, Jr.
(74) *Attorney, Agent, or Firm* — Cantor Colburn LLP

(57) ABSTRACT

An articulating structure that bends by relative movement of a plurality of segments connected in series, includes a first segment and a second segment arranged in contact with each other, wherein the first segment has a first front rolling contact surface, and the second segment has a second rear rolling contact surface in line contact with the first front rolling contact surface on a first direction contact line, the first segment has a projection protruding forward from the first front rolling contact surface, and the second segment has a coupling element recessed in the second rear rolling contact surface, wherein the projection is inserted into the coupling element, the first segment and the second segment make a relative rolling movement for translation of the first direction contact line while maintaining the line contact, and the projection supports the first segment and the second segment for the first direction.

13 Claims, 14 Drawing Sheets

(56) References Cited

U.S. PATENT DOCUMENTS

| | | | |
|---|---|---|---|
| 5,755,731 A * | 5/1998 | Grinberg | A61B 17/32002 604/22 |
| 6,682,493 B2 * | 1/2004 | Mirigian | A61M 25/09 600/585 |
| 6,949,101 B2 * | 9/2005 | McCleary | A61B 17/1668 606/80 |
| 7,874,980 B2 * | 1/2011 | Sonnenschein | A61B 1/008 600/141 |
| 8,376,865 B2 * | 2/2013 | Forster | A61M 25/0113 464/78 |
| 9,144,370 B2 * | 9/2015 | Kato | A61B 1/0055 |
| 9,572,628 B2 * | 2/2017 | Zubiate | A61B 34/30 |
| 9,981,392 B2 * | 5/2018 | Kim | B25J 18/06 |
| 2005/0113640 A1 * | 5/2005 | Saadat | A61B 17/00234 600/106 |
| 2012/0190924 A1 * | 7/2012 | Tseng | A61B 1/00066 600/127 |
| 2012/0197241 A1 * | 8/2012 | Golden | A61B 1/008 606/1 |
| 2014/0148787 A1 | 5/2014 | Forster et al. | |
| 2017/0120457 A1 | 5/2017 | Saraliev et al. | |
| 2018/0200895 A1 | 7/2018 | Kan | |

FOREIGN PATENT DOCUMENTS

| | | |
|---|---|---|
| KR | 101427322 B1 | 8/2014 |
| WO | 2014201538 A1 | 12/2014 |

\* cited by examiner

ARTICULATING STRUCTURE USING ROLLING JOINT AND PROJECTION MEMBER, AND TUBE INSERT DEVICE HAVING THE SAME

CROSS-REFERENCE TO RELATED APPLICATION

This application claims priority to Korean Patent Application No. 10-2019-0056877, filed on May 15, 2019, and all the benefits accruing therefrom under 35 U.S.C. § 119, the contents of which in its entirety are herein incorporated by reference.

BACKGROUND

1. Field

The present disclosure relates to an articulating structure and a tube insert device having the same, and more particularly, to an articulating structure using both rolling joint and projection member and a tube insert device having the same.

[Description of Government-Funded Research and Development]

This research is conducted by Hanyang Digitech, and funded by robotics industry core technology development (R&D) of Korea Evaluation Institute of Industrial Technology, Ministry of Trade, Industry and Energy, Republic of Korea (Development of flexible joint single passage surgical robotic technology based on fluoroscopy-induced endoscopy for transoral and laparoscopic surgery, No. 1415162841).

2. Description of the Related Art

A typical example of a tube insert device used to perform a predetermined operation by inserting a long hollow tube into a narrow space is microsurgical instruments for minimally invasive surgery.

The minimally invasive surgery is a surgery that is performed through a minimal incision as compared to open surgery, and it has advantages such as small incisions, less or no scars or after effects and fast recovery.

The microsurgical instruments for minimally invasive surgery are used to perform a predetermined operation such as surgery in a narrow space, so its control has been studied so much.

Particularly, suggests have been various types of articulating structures for locally changing the direction of an end effector positioned at the front end of the microsurgical instrument.

It is known that the articulating structure typically has a structure in which a plurality of segments is connected in series, and steering is accomplished by the relative movements of adjacent segments.

The plurality of segments is generally fixed in place with respect to each other by pulling using a steering means, for example, a wire, but when the segments are only supported by the wire without any other fixing means, the segments may be separated by an unexpected external force.

Accordingly, as in US Patent Publication No. 2014/0148787 ("Patent Literature 1"), for example, a structure of supporting each segment by a projection structure is employed. In US Patent Publication No. 2014/0148787, the projection structure serves as a hinge that is the center of pivot in the relative movements of the segments.

The two segments cannot smoothly move due to loads focused on the hinge during movements due to the fixed projection structure. Additionally, the projection structure of Patent Literature 1 fails to support a side for a direction approximately perpendicular to the bending direction of the joint, and thus its side stiffness is weak.

SUMMARY

The present disclosure is designed to solve the above-described problem, and therefore the present disclosure is directed to providing an articulating joint for allowing smooth and precise steering and maintaining tight coupling between a plurality of segments and a tube insert device having the same.

To achieve the above-described object, according to an aspect of the present disclosure, there is provided an articulating structure that bends by relative movement of a plurality of segments connected in series, the articulating structure including a first segment and a second segment arranged in contact with each other, wherein the first segment has a first front rolling contact surface, and the second segment has a second rear rolling contact surface in line contact with the first front rolling contact surface on a contact line ("a first direction contact line") extending in a first direction, the first segment has a projection protruding forward from the first front rolling contact surface, and the second segment has a coupling element recessed in the second rear rolling contact surface, wherein the projection is inserted into the coupling element, the first segment and the second segment make a relative rolling movement for translation of the first direction contact line while maintaining the line contact of the first front rolling contact surface and the second rear rolling contact surface, and the projection supports the first segment and the second segment for the first direction.

According to an embodiment, the projection may be formed with such a length as to prevent a front end of the projection from coming into contact with a bottom surface of the coupling element while keeping at least part of the projection inserted into the coupling element during the rolling movement.

According to an embodiment, two projections may be spaced in the first direction apart from a center of the first segment on the first front rolling contact surface.

According to an embodiment, the projection may have a width of a second direction perpendicular to the first direction, the coupling element may have a width of the second direction, and the width of the projection may be smaller than the width of the coupling element.

According to an embodiment, the plurality of segments may have a wire connection hole passing through front and rear surfaces of each segment, and a wire passage groove through which a wire passes may be formed on an outer surface of the projection.

According to an embodiment, when the articulating structure is placed in a straight line, a wire may pass through the wire connection holes of each segment arranged such that the wire connection holes are aligned in a lengthwise direction of the articulating structure, and the plurality of segments may make the relative movement by pulling or releasing the wire in the lengthwise direction of the articulating structure.

According to an embodiment, the wire connection holes may include a pair of first direction wire connection holes arranged in the first direction and a pair of second direction wire connection holes arranged in the second direction.

According to an embodiment, the first front rolling contact surface and the second rear rolling contact surface may be formed as part of a circumference of a circular cylinder.

According to an embodiment, an outer surface and an inner surface of the projection may be formed as a convex surface that curves outward in a radial direction of the first segment.

According to an embodiment, the articulating structure may include a third segment positioned in contact with the second segment, the second segment may have a second front rolling contact surface opposite the second rear rolling contact surface, the third segment may have a third rear rolling contact surface in line contact with the second front rolling contact surface, the second segment may have a projection protruding forward from the second front rolling contact surface, and the third segment may have a coupling element recessed in the third rear rolling contact surface, wherein the projection is inserted into the coupling element.

According to an embodiment, the second front rolling contact surface and the third rear rolling contact surface may be in line contact with each other on a contact line ("a second direction contact line") extending in the second direction perpendicular to the first direction, the second segment and the third segment may make a relative rolling movement for translation of the second direction contact line while maintaining the line contact of the second front rolling contact surface and the third rear rolling contact surface, and the projection of the second segment may support the second segment and the third segment for the second direction.

According to an embodiment, a tool connection hole passing through upper and lower surfaces of each segment may be formed at a center of the plurality of segments.

According to another aspect of the present disclosure, there is provided a tube insert device including an elongated tube, and the articulating structure connected to a front end of the tube.

DETAILED DESCRIPTION

Figure 1:
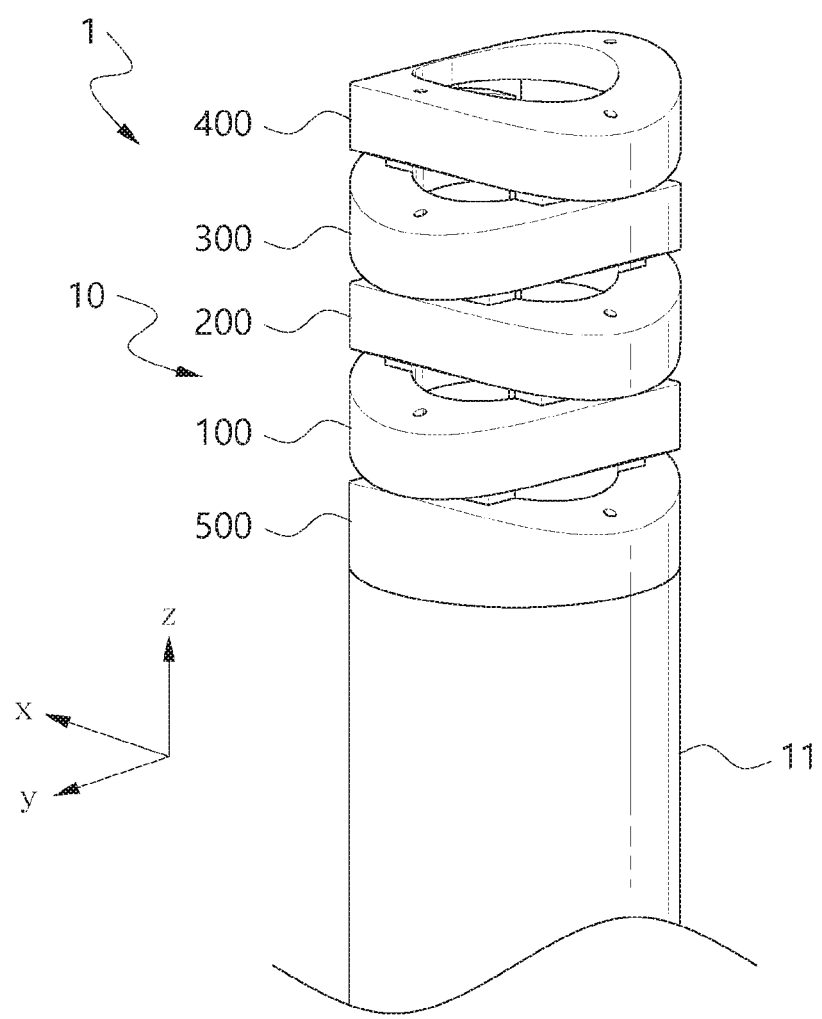
FIG. 1 is a perspective view of a surgical instrument having an articulating structure according to an embodiment of the present disclosure.

Hereinafter, exemplary embodiments of the present disclosure will be described with reference to the accompanying drawings. The present disclosure is described with reference to the embodiments shown in the drawings, but this is described as one embodiment, and the technical spirit of the present disclosure and its essential elements and operation are not limited thereto.

FIG. 1 is a perspective view of a surgical instrument 1 having an articulating structure 10 according to an embodiment of the present disclosure.

As shown in FIG. 1, the articulating structure 10 includes a plurality of segments 100, 200, 300, 400, 500 connected in series. As described below, the articulating structure 10 has a structure such that it is steered by the bending by relative movements of the plurality of segments 100, 200, 300, 400, 500.

According to this embodiment, for example, the articulating structure 10 is used as an end effector of the tube insert device 1.

For example, the tube insert device 1 is a microsurgical instrument that is inserted into the body to perform various types of surgeries, and includes a tube 11 that extends longitudinally to be inserted into the body, and the articulating structure 10 according to this embodiment is attached to the front end. However, the tube insert device 1 according to this embodiment is not limited to a microsurgical instrument, and may be used in various types of tasks requiring a tube that is so thin and long as to be inserted into a narrow orifice.

The articulating structure 10 makes bending movements at the front end of the tube 11 to allow stable steering of the tip of the tube insert device 1 in all directions with high curvature, thereby enhancing the stability and convenience of the non-invasive surgery.

As shown in FIG. 1, the articulating structure 10 includes a proximal segment (a fifth segment) 500, a first segment 100 positioned in series in contact with the fifth segment 500, a second segment 200 positioned in series in contact with the first segment 100, a third segment 300 positioned in series in contact with the second segment 200 and a distal segment (a fourth segment) 400 positioned in series in contact with the third segment 300.

In the specification, when the first to fifth segments 100 to 500 are arranged in a straight line, a direction of a line connecting the centers of the first to fifth segments 100 to 500 is defined as a lengthwise direction Z of the articulating structure 10.

Figure 2A:
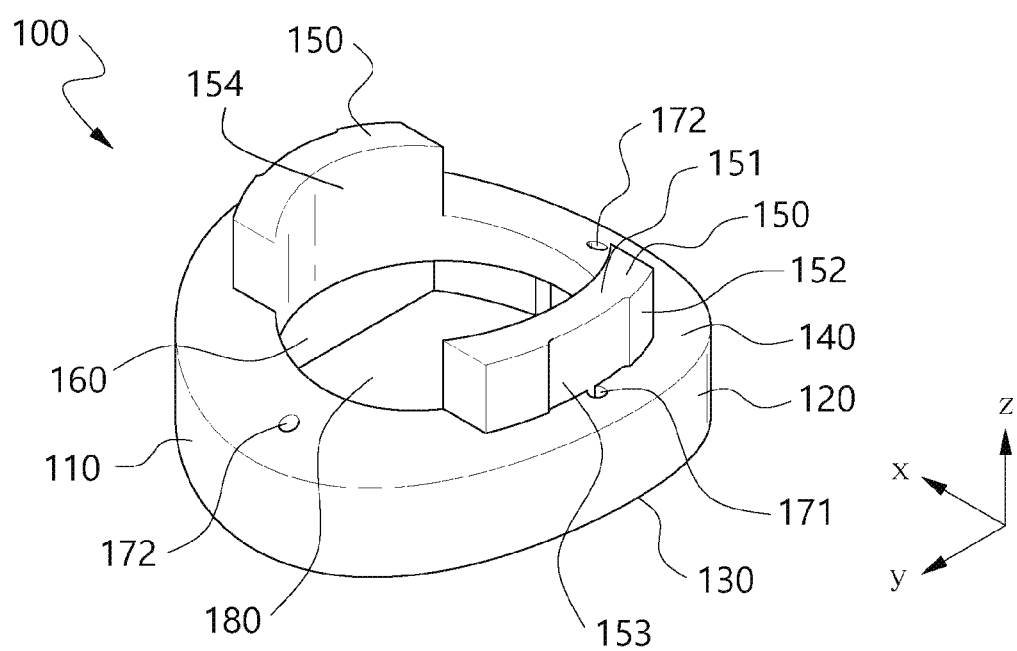
FIGS. 2A to 2E are diagrams showing a first segment of an articulating structure.
Figure 2B:
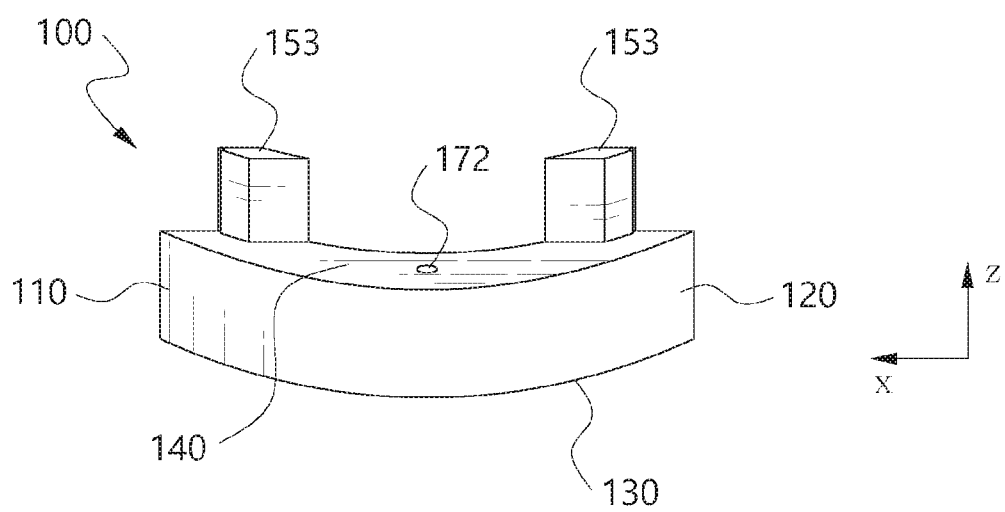
Figure 2C:
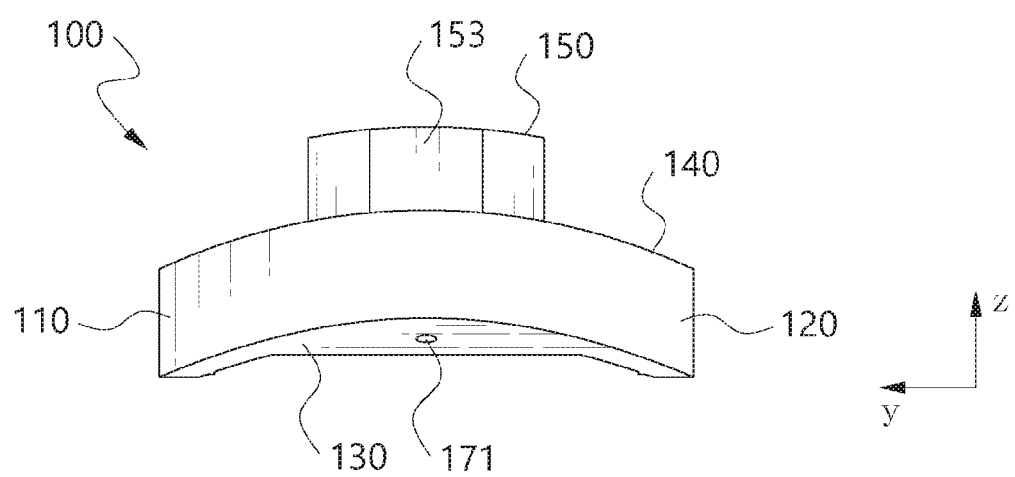
Figure 2D:
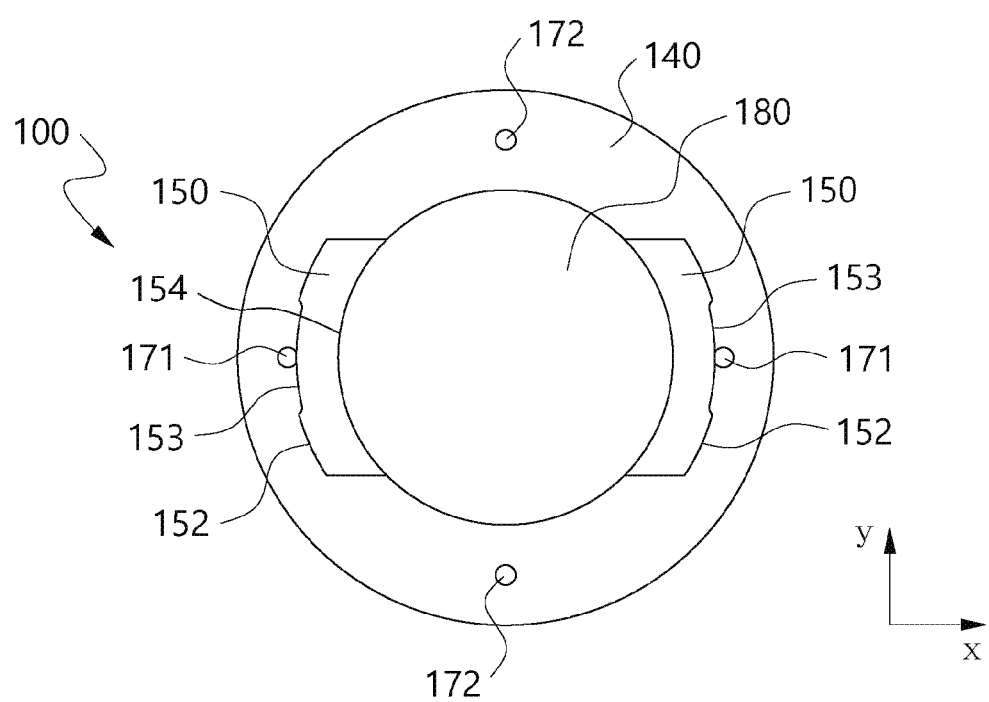
Figure 2E:
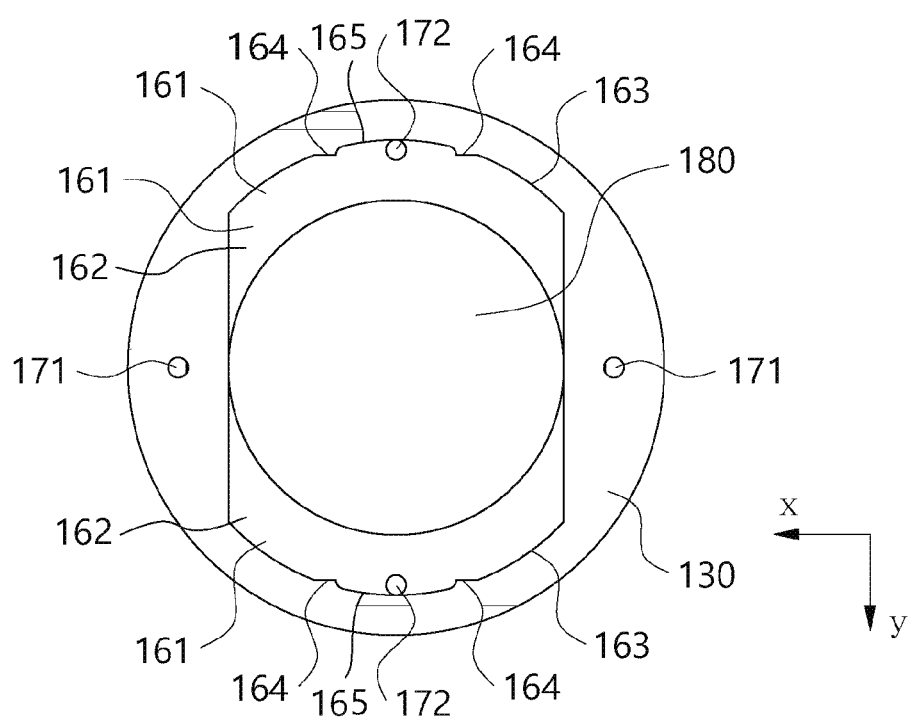

FIGS. 2A to 2E are diagrams showing the first segment 100 of the articulating structure 10. FIG. 2A is a perspective view of the first segment 100, FIG. 2B is a front view of the first segment 100 and FIG. 2C is a side view of the first segment 100. FIG. 2D is a plane view of the first segment 100 and FIG. 2E is a bottom view of the first segment 100.

As shown in FIGS. 2A to 2E, the first segment 100 includes a body 110 having a predetermined thickness, projection 150 protruding frontward from the front surface of the body 110, and coupling element 161 recessed in the rear surface of the body 110.

According to this embodiment, the body 110 has a first front rolling contact surface 140 on the front surface, and a first rear rolling contact surface 130 on the rear surface.

In this embodiment, "front" indicates a distal direction of the articulating structure 10, and "rear" indicates a proximal direction of the articulating structure 10. When the articulating structure 10 is placed in a straight line, the front-rear direction of each segment matches the lengthwise direction Z of the articulating structure 10. However, "front" and "rear" are relative terms, and on the contrary, when the distal side of the articulating structure 10 is defined as "rear", the proximal side is defined as "front".

As clearly shown in FIG. 2C, according to this embodiment, the first front rolling contact surface 140 is part of the circumference of a circular cylinder around an imaginary axis line extending in a first direction X, spaced apart a predetermined distance in the rear direction from the first front rolling contact surface 140.

Also, as clearly shown in FIG. 2B, according to this embodiment, the first rear rolling contact surface 130 is part of the circumference of a circular cylinder around an imaginary axis line extending in a second direction Y perpendicular to the first direction X, spaced apart a predetermined distance in the front direction from the first rear rolling contact surface 130.

That is, the first front rolling contact surface 140 and the first rear rolling contact surface 130 are twisted at 90° intervals.

The side 120 of the body 110 is formed as a circumferential surface of a circular cylinder, and thus when the first segment 100 is viewed from the front side or the rear side, the body 110 forms a circle around the center of the first segment 100.

The body 110 has a plurality of wire connection holes 171, 172 passing through the body 110 in the front-rear direction. According to this embodiment, four wire connection holes 171, 172 are formed, and the wire connection holes 171, 172 include a pair of first direction wire connection holes 171 arranged in the first direction X and a pair of second direction wire connection holes 172 arranged in the second direction Y.

A tool connection hole 180 passing through the body 110 in the front-rear direction is formed at the center of the first segment 100 surrounded by the four wire connection holes 171, 172.

According to this embodiment, the first front rolling contact surface 140 has two projections 150 standing forward from the first segment 100. The two projections 150 are spaced apart in the first direction X from the center of the first segment 100.

As shown in FIG. 2D, the two projections 150 are positioned between the two first direction wire connection holes 171 arranged in the first direction X.

The projection 150 has the shape of a column that extends to a height forward from the first front rolling contact surface 140 and has the width of the second direction Y larger than the width of the first direction X.

According to this embodiment, an outer surface 152 and an inner surface 154 of the projection 150 is a convex surface that curves outward in the radial direction of the first segment 100. In more detail, according to this embodiment, the outer surface 152 and the inner surface 154 of the projection 150 are part of the circumference of a circular cylinder that is concentric with the side 120 of the first segment 100. That is, a circumferential surface of the circular cylinder that is concentric with the side 120 of the first segment 100 is defined by extending each of the outer surface 152 and the inner surface 154 in the circumferential direction.

The inner surface 154 of the projection 150 has the same radius as the tool connection hole 180, and smoothly connects to the inner surface of the tool connection hole 180 without a step (see FIG. 2A).

A wire passage groove 153 recessed inward in the radial direction of the first segment 100 is formed on the outer surface 152 of the projection 150. The wire passage groove 153 is formed in substantially contact with the first direction wire connection hole 171 when viewed in the front-rear direction of the first segment 100. If the outer surface 152 of the projection 150 is formed as part of the circumference of the circular cylinder without forming the wire passage groove 153, the outer surface 152 of the projection 150 extends, covering part of the first direction wire connection hole 171. According to this embodiment, when the wire passage groove 153 is formed concavely, the opening of the first direction wire connection hole 171 is not covered by the projection 150 and is exposed through the first front rolling contact surface 140.

According to this embodiment, when the inner surface 154 of the projection 150 is formed as a curved surface (having the same radius as the tool connection hole 180), it is possible to increase the radius of the tool connection hole 180 while ensuring a predetermined length or more of the width of the second direction Y of the projection 150. That is, it is possible to increase the size of the tool connection hole 180 so that the tool connection hole 180 is as large as possible within the limited radius range of the first segment 100, thereby allowing a sufficient space through which the tool passes.

In contrast, when the outer surface 152 of the projection 150 is formed as a curved surface, it is possible to reduce the radius of the first segment 100 to the maximum extent while ensuring a predetermined length or more of the width of the second direction Y of the projection 150. Moreover, when the wire passage groove 153 is formed by cutting out part of the outer surface 152 of the projection 150, the first direction wire connection hole 171 may be formed closer to the center of the first segment 100, thereby reducing the radius of the first segment 100.

As shown in FIG. 2E, the first rear rolling contact surface 130 of the first segment 100 has a rear groove 160. According to this embodiment, the rear groove 160 has a shape that extends longitudinally in the second direction Y by 90° relative to the arrangement direction of the two projections 150 (the first direction X).

The rear groove 160 is a groove that is open to the bottom at the center so that it is in communication with the tool connection hole 180, and is closed at two ends. According to this embodiment, each of the two ends of the rear groove 160 is a coupling element 161. That is, according to this embodiment, the first segment 100 has two coupling elements 161 recessed in the first rear rolling contact surface 130, and the two coupling elements 161 are arranged in the second direction Y by 90° relative to the two projections 150.

The coupling element 161 has a depth that is smaller than the height of the body 110 of the first segment 100 and larger than the length of the projection 150.

The coupling element 161 has a bottom surface 162 facing the opening of the coupling element 161, and an inner surface 163 formed in the front-rear direction of the first segment 100.

According to this embodiment, the inner surface 163 of the coupling element 161 is part of the circumference of the circular cylinder that is concentric with the projection 150 (the side 120 of the first segment 100).

The second wire connection hole 172 is formed such that it passes through the bottom surface 162 of the coupling element 161, and the second wire connection hole 172 is in substantially contact with the inner surface 163 of the coupling element 161 when viewed in the front-rear direction.

The inner surface 163 of the coupling element 161 has two protrusions 164. In this embodiment, the inner surface 163 part between the two protrusions 164 is a wire passage part 165, and the length of the wire passage part 165 is approximately equal to the length of the wire passage groove 153 of the projection 150.

The second wire connection hole 172 is formed such that it passes through the bottom surface 162 of the coupling element 161 between the two protrusions 164, and the second wire connection hole 172 is substantially in contact with the wire passage part 165 of the coupling element 161 when viewed in the front-rear direction.

The first segment 100 configured as described above is positioned in contact with the second segment 200 in the front-rear direction, and they are coupled to each other.

According to this embodiment, the configuration of the second segment 200 is substantially the same as the first segment 100. The second segment 200 is described by replacing some letters and numbers in FIGS. 2A to 2E and the above description of FIGS. 2A to 2E, such as "first" with "second", 100 and subsequent numbers with 200 and subsequent numbers, the first direction X with the second direction Y and the second direction Y with the first direction X. Accordingly, in the description of the configuration of the second segment 200, redundant descriptions are omitted herein.

Figure 3:
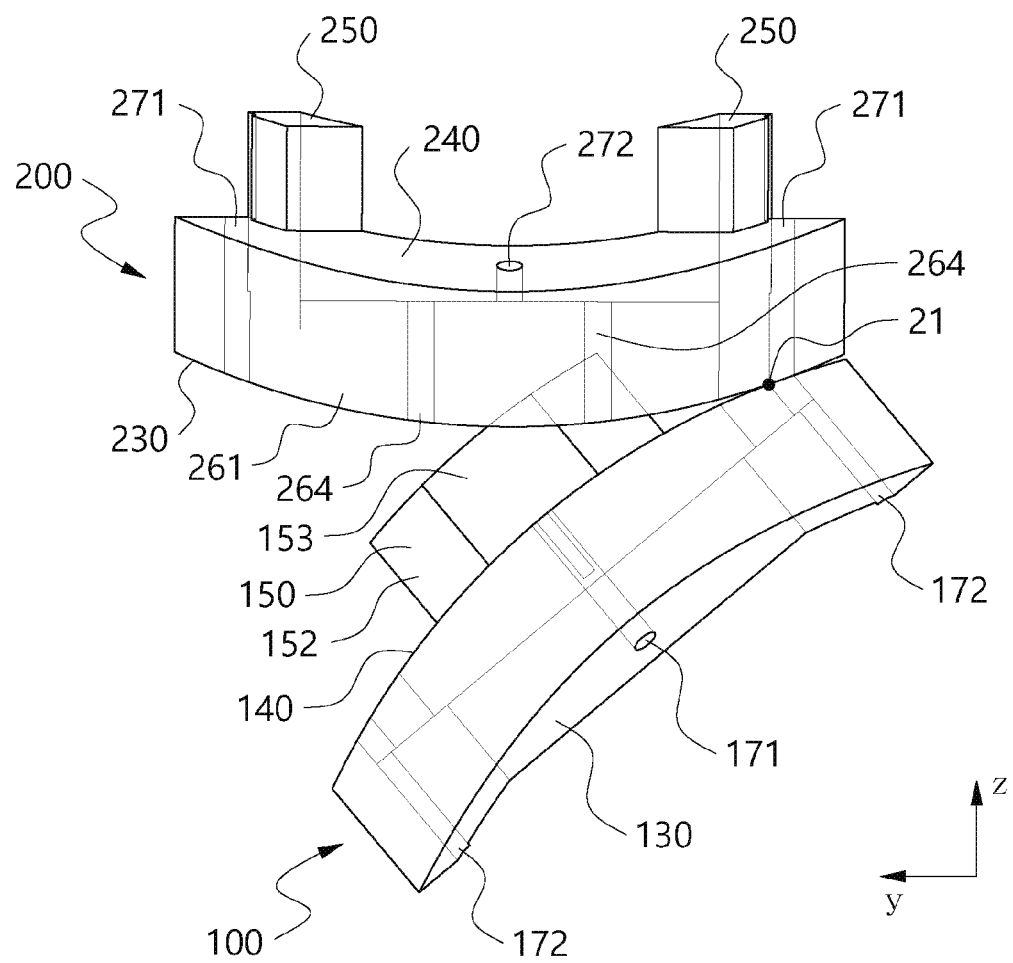
FIGS. 3 and 4 are assembled state diagrams of a first segment and a second segment of an articulating structure.
Figure 4:
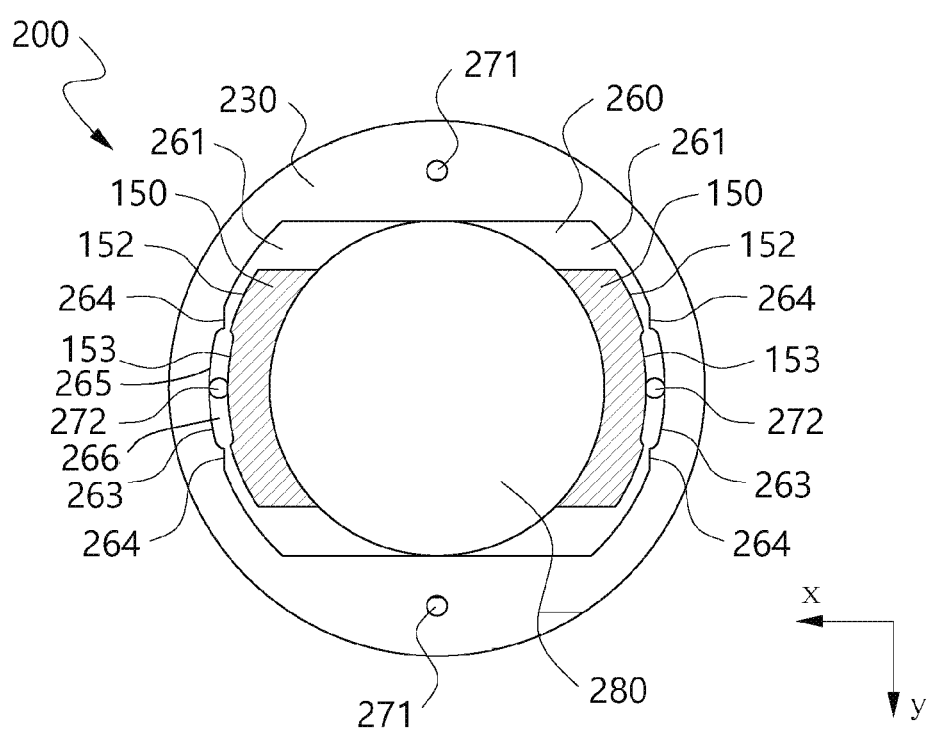

FIGS. 3 and 4 show the first segment 100 and the second segment 200 coupled to each other. FIG. 3 is an operational state diagram of the first segment 100 and the second segment 200 flexed relative to each other. FIG. 4 is a diagram showing the first segment 100 and the second segment 200 coupled to each other when viewed forward from the rear side, and in the first segment 100, only the projection 150 is shown in FIG. 4 for convenience of description.

As shown in FIG. 3, the first segment 100 and the second segment 200 arranged in the front-rear direction are connected to bring the first front rolling contact surface 140 of the first segment 100 and a second rear rolling contact surface 230 of the second segment 200 into contact with each other.

As described above, the first front rolling contact surface 140 is part of the circumference of the circular cylinder having the center axis on the rear side, and the second rear rolling contact surface 230 is part of the circumference of the circular cylinder having the center axis on the front side, and thus the contact surfaces (the first front rolling contact surface 140 and the second rear rolling contact surface 230) between the first segment 100 and the second segment 200 are in line contact with each other on a contact line ("a first direction contact line") 21 extending in the first direction X.

In this instance, the projections 150 of the first segment 100 are each inserted into coupling elements 261 of the second segment 200.

As shown in FIG. 4, the width of the second direction Y of the projection 150 is smaller than the width of the coupling element 261.

When the first segment 100 and the second segment 200 are arranged in a straight line without relative bending to form the first direction contact line 21 at the center of the first front rolling contact surface 140 and the second rear rolling contact surface 230 (initial state), the projection 150 is disposed at the center of the coupling element 261 (see FIG. 1).

The outer surface 152 of the projection 150 and an inner surface 263 of the coupling element 261 are positioned with a slight gap. In this instance, the wire passage groove 153 of the projection 150 and a wire passage part 265 of the coupling element 261 are positioned facing each other. A wire passageway 266 that is a larger space than a space between the outer surface 152 of the projection 150 and the inner surface 263 of the coupling element 261 is formed between the wire passage groove 153 and the wire passage part 265. The wire passageway 266 is a space in the shape of an approximately rectangular column having the width of the second direction Y larger than the width of the first direction X in the initial state, and the width of the first direction X of the wire passageway 266 is substantially equal to the radius of a first wire connection hole 272 of the second segment 200.

As shown in FIG. 3, according to this embodiment, as described below, when a force is applied to one side of the second segment 200 by a driving means such as a wire, the first segment 100 and the second segment 200 make relative rolling movements, and accordingly the second segment 200 is slanted with respect o the first segment 100. In this instance, the two segments 100, 200 make rolling movements with the translation of the first direction contact line 21 in approximately the second direction Y while maintaining the line contact.

As described above, the articulating structure 10 bends by relative rolling movements between adjacent segments in line contact with each other, thereby minimizing the contact area between the segments of the joint and dissipating loads at the contact point, hence allowing smooth and high curvature bending movements with a small force. Additionally, as the contact between the two segments 100, 200 is maintained, the entire length of the articulating structure 10 reduces.

According to this embodiment, the first front rolling contact surface 140 of the first segment 100 and the second rear rolling contact surface 230 of the second segment 200 in contact with each other are formed such that the entire corresponding surface is part of the circumference of the circular cylinder. Accordingly, it is possible to minimize an area irrelevant to rolling movement, thereby reducing the diameter of the articulating structure 10. However, when not only a central tool connection hole 570 but also an additional auxiliary tool connection hole is formed, the first front rolling contact surface 140 and the second rear rolling contact surface 230 may be part of the front surface of the first segment 100 and the rear surface of the second segment 200 respectively.

Additionally, according to this embodiment, the first front rolling contact surface 140 of the first segment 100 and the second rear rolling contact surface 230 of the second segment 200 are part of the circumference of the circular cylinders having the same radius (that is to say, the curvature of the first front rolling contact surface 140 is equal to the curvature of the second segment 200). Accordingly, it is possible to simplify the computation for steering control of the articulating structure 10.

According to this embodiment, the second direction Y of the projection 150 is smaller than the width of the coupling element 261, and the width of the projection 150 is set such that the top edge of the projection 150 does not comes into contact with an inner surface of a rear groove 260 of the second segment 200 during rolling movements of the two segments 100, 200. That is, when the two segments 100, 200 are flexed more than a predetermined angle, as shown in FIG. 3, the top edge on one side of the projection 150 may be separated from the coupling element 261. Accordingly, the two segments 100, 200 may make rolling movements to the maximum bend in the initial state without interference of the projection 150.

However, when the two segments 100, 200 are flexed at the predetermined angle, the top edge of the projection 150 comes into contact with the inner surface of the rear groove 260 of the second segment 200 to stop the second segment 200 from being further slanted with respect to the first segment 100, thereby adjusting the maximum bending angle of the articulating structure 10.

According to this embodiment, the projection 150 of the first segment 100 is long so that a front end surface 151 of the projection 150 does not come into contact with a bottom surface 262 of the coupling element 261 of the second segment 200 not only in the initial state but also even at the moment that the projection 150 and the bottom surface 262 of the coupling element 261 is closer to each other than the distance of the initial state when the projection 150 is slanted with respect to the coupling element 261.

Accordingly, it is possible to prevent the projection 150 from coming into contact with the bottom surface 262 of the coupling element 261 and raising up the second segment 200, thereby allowing the two segments 100, 200 to make rolling movements while maintaining the line contact.

As described above, the projection 150 of the first segment 100 is formed with such length so as not to hinder the relative rolling movements of the first segment 100 and the second segment 200, but as shown in FIG. 3, the length of the projection 150 is set such that even when the first segment 100 and the second segment 200 are flexed to the maximum by the rolling movements, at least part of the projection 150 is still inserted into the coupling element 261.

That is, the projection 150 supports the coupling element 261 of the second segment 200 in the first direction X, and thus it is possible to prevent the first segment 100 and the second segment 200 from being misaligned or separated in the first direction X during rolling movements. In more detail, according to this embodiment, the two projections 150 support such that while the outer surface 152 of the projections 150 is in contact with the inner surface 263 of the coupling elements 261 of the second segment 200, the left projection 150 resists a force applied from left to right, and the right projection 150 resists a force applied from right to left in FIG. 4. As the two projections 150 are formed as described above, a tool connection hole 280 may be formed between the projections 150.

According to this embodiment, the articulating structure 10 has the rolling joint having a smooth moving characteristic and can maintain the stiffness of the joint for the first direction X by the support of the projections.

According to the connection of the first segment 100 and the second segment 200 as described above, the articulating structure 10 may bend in the second direction Y.

According to this embodiment, to provide a 2 degree of freedom to the articulating structure 10, the third segment 300 is additionally connected to the second segment 200.

According to this embodiment, the third segment 300 is the same as the first segment 100. The second segment 200 is described by replacing some letters and numbers in FIGS. 2A to 2E and the above description of FIGS. 2A to 2E, such as "first" with "third" and 100 and subsequent numbers with 300 and subsequent numbers. Accordingly, in the description of the configuration of the third segment 300, redundant descriptions are omitted herein.

As shown in FIG. 1, the third segment 300 is positioned in contact with the second segment 200 on the front side of the second segment 200. In this instance, a second front rolling contact surface 240 of the second segment 200 and a third rear rolling contact surface 330 of the third segment 300 contact each other, and the second front rolling contact surface 240 and the third rear rolling contact surface 330 are in line contact with each other on a contact line ("a second direction contact line") 22 extending in the second direction Y (see FIGS. 8 and 10).

A projection 250 of the second segment 200 is inserted into a coupling element 361 of the third segment 300.

The second segment 200 and the third segment 300 connected as described above make relative rolling movements in the first direction X with the translation of the second direction contact line 22 while maintaining the line contact. The movements of the second segment 200 and the third segment 300 will be described in more detail below.

According to this embodiment, segments of the same structure as the second segment 200 may be further connected on the front side of the third segment 300. That is, the articulating structure 10 according to this embodiment may increase the length as much as desired by connecting the segments of the same structure as the first segment 100 to the front side of the first segment 100 one after another by 90°.

To stop extending the length of the articulating structure 10 forward, the articulating structure 10 may include a distal segment connected to the foremost.

Figure 5:
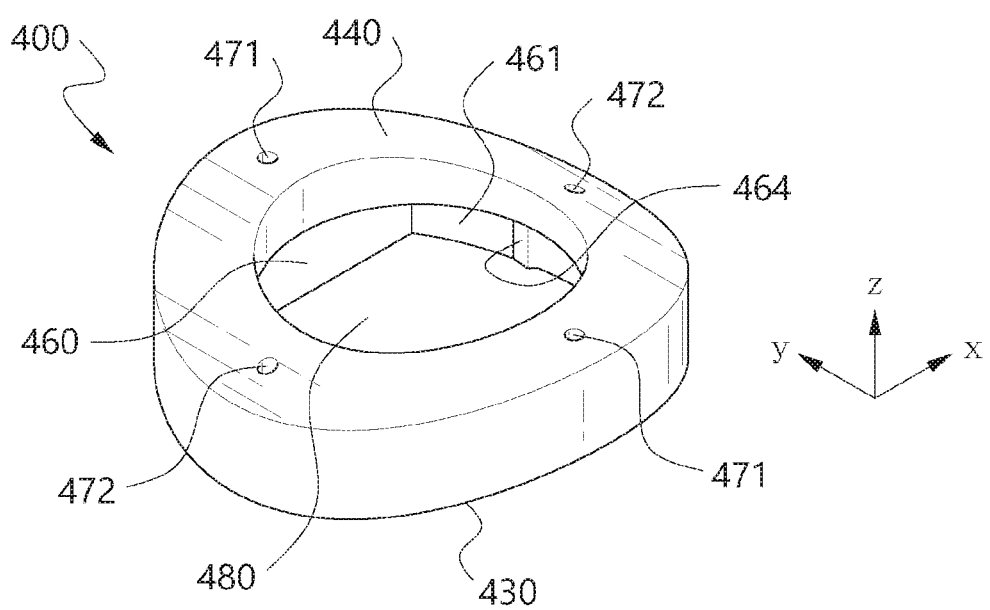
FIG. 5 is a perspective of a fourth segment of an articulating structure.

FIG. 5 is a perspective view of the distal segment or the fourth segment 400 disposed at the most distal position of the articulating structure 10.

Referring to FIG. 5, the fourth segment 400 according to this embodiment has the same configuration as the second segment 200 except that there is no projection on the front surface. Here, the front surface of the fourth segment 400 is formed as a fourth front rolling contact surface 440 that forms part of the circumference of a circular cylinder, but the front surface of the fourth segment 400, namely, the most distal surface of the articulating structure 10 may be formed as a flat surface.

As shown in FIG. 1, the fourth segment 400 is positioned in contact with the third segment 300 on the front side of the third segment 300. In this instance, the third front rolling contact surface 340 of the third segment 300 and a fourth rear rolling contact surface 430 of the fourth segment 400 contact each other, and the third front rolling contact surface 340 and the fourth rear rolling contact surface 430 are in line contact with each other on the first direction contact line 21 (see FIGS. 8 and 10).

A projection 350 of the third segment 300 is inserted into a coupling element 461 of the fourth segment 400.

The third segment 300 and the fourth segment 400 connected as described above make relative rolling movements in the second direction Y with the translation of the first direction contact line 21 while maintaining the line contact. The movements of the third segment 300 and the fourth segment 400 will be described in more detail below.

Figure 6:
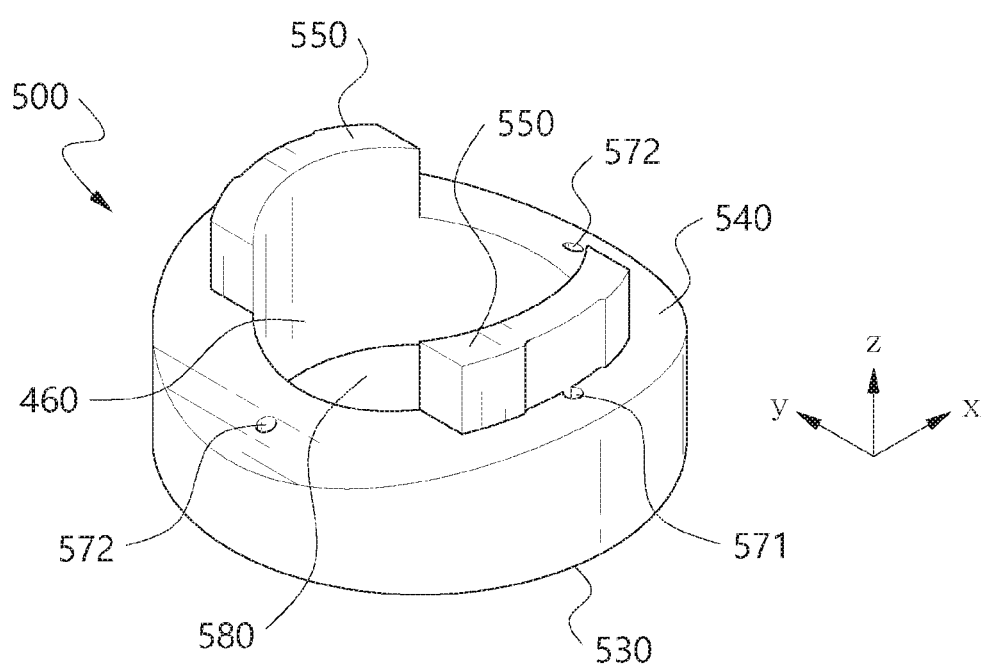
FIG. 6 is a perspective view of a fifth segment of an articulating structure.

Alternatively, other segment may be connected to the rear side of the first segment 100. FIG. 6 is a perspective view of the fifth segment 500 connected to the rear side of the first segment 100.

As shown in FIGS. 1 and 6, the fifth segment 500 is a proximal segment disposed at the most proximal position of the articulating structure 10.

Referring to FIG. 6, the fifth segment 500 according to this embodiment basically has similar configuration to the second segment 200. However, the fifth segment 500 includes a body 510 having a slight larger thickness than the other segments, and a rear surface 530 is flat and thus a rear rolling contact surface is not formed. Accordingly, it is easy to couple to the front end of the cylindrical tube 11.

As shown in FIG. 1, the fifth segment 500 is positioned in contact with the first segment 100 on the rear side of the first segment 100. In this instance, the first rear rolling contact surface 130 of the first segment 100 and a fifth front rolling contact surface 540 of the fifth segment 500 contact each other, and the first rear rolling contact surface 130 and the fifth front rolling contact surface 540 are in line contact with each other on the second direction contact line 22 (see FIGS. 8 and 10). A projection 550 of the fifth segment 500 is inserted into the coupling element 161 of the first segment 100.

In the same way as the second segment 200 and the third segment 300, the first segment 100 and the fifth segment 500 connected as described above make rolling movements in the first direction X with the translation of the second direction contact line 22 while maintaining the line contact. The movements of the first segment 100 and the fifth segment 500 will be also described in more detail below.

Likewise, instead of the fifth segment 500, the articulating structure 10 may increase the length as much as desired by connecting segments of the same structure as the first segment 100 to the rear side of the first segment 100 one after another by 90°.

Hereinafter, the steering operation of the articulating structure 10 configured as described above will be described with reference to FIGS. 7 to 10.

Figure 7:
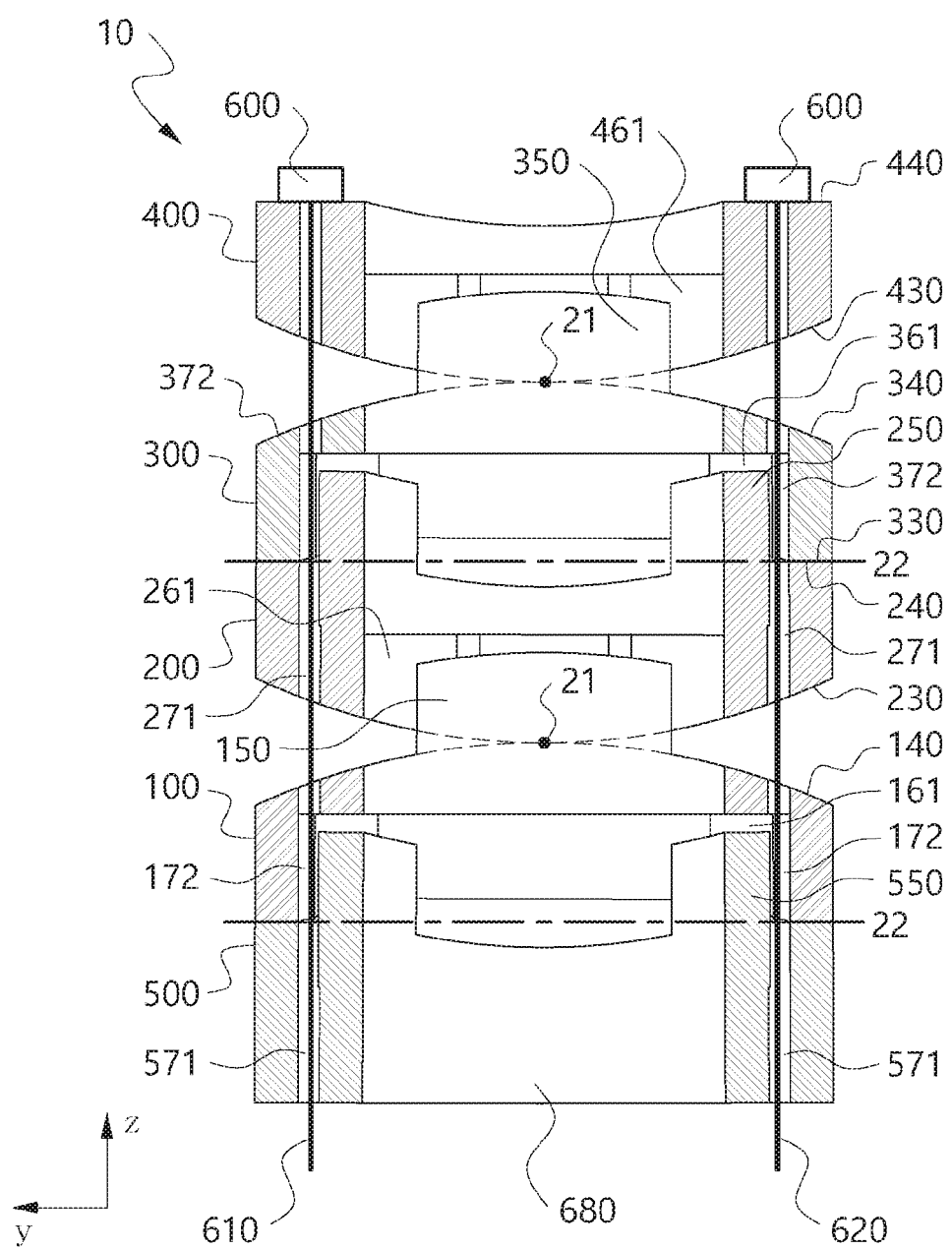
FIG. 7 is a cross-sectional view of an articulating structure when viewed from a first direction.
Figure 8:
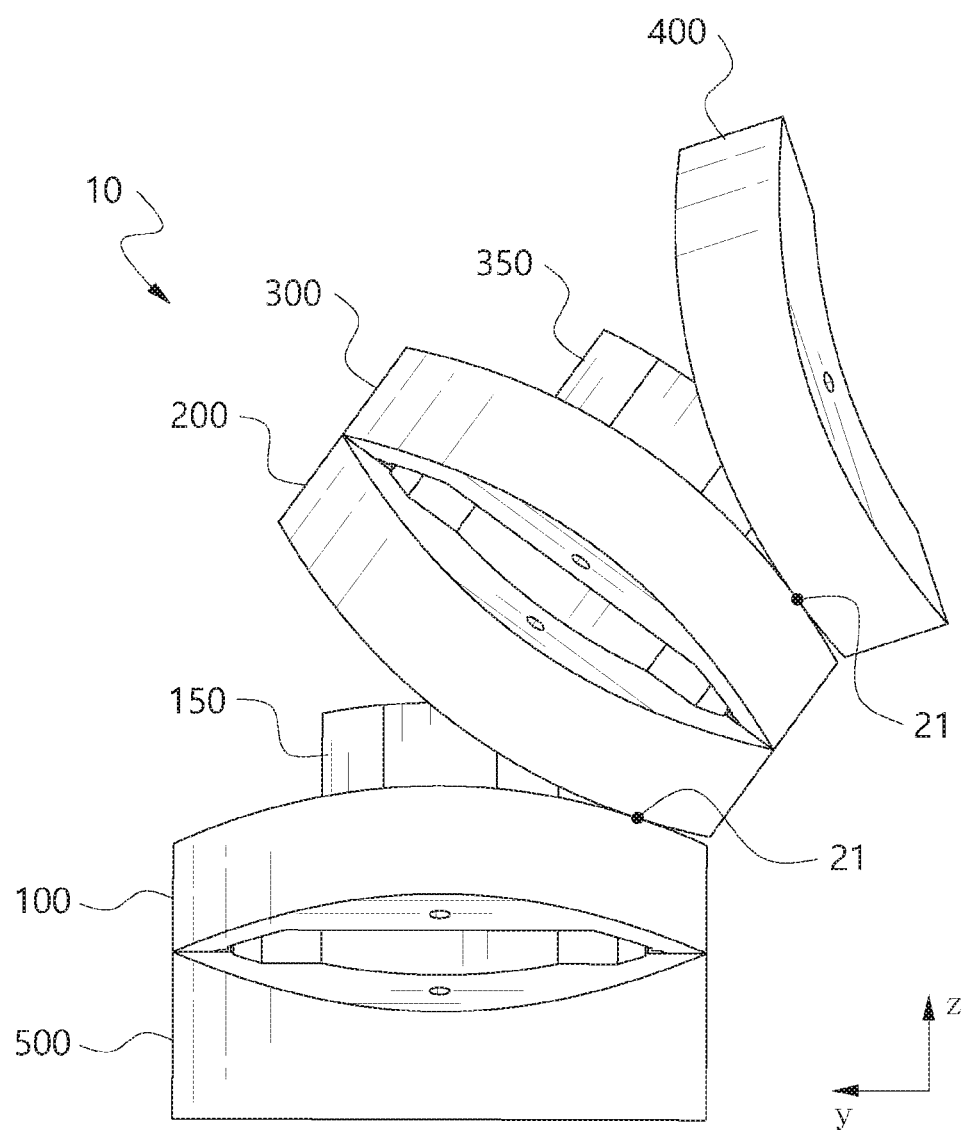
FIG. 8 is an operational state diagram of an articulating structure when viewed from a first direction.

FIG. 7 is a cross-sectional view of the articulating structure 10 when viewed in the first direction X, and FIG. 8 is an operational state diagram of the articulating structure 10 when viewed in the first direction X.

As shown in FIG. 7, in the initial state in which the articulating structure 10 is placed in a straight line, the second wire connection holes 172, 271, 372, 471, 571 formed in each segment 100 to 500 are aligned in the lengthwise direction Z of the articulating structure 10, forming a substantially linear wire connection passage.

Each wire 610, 620 passes through the two second wire connection holes 172, 271, 372, 471, 571 arranged in the second direction Y.

According to this embodiment, as the wire connection hole passes through the front and rear surfaces of the body of each segment, the wire is not exposed to the outside of the articulating structure 10 (the tube insert device 1) and is hidden inside. Accordingly, it is possible to avoid the interference of the wire with many tissues in the body. Moreover, it is possible to reduce the diameter of the articulating structure 10.

As shown in FIG. 7, for example, the front end of the wires 610, 620 is connected to a head 600 having a larger diameter than the second wire connection hole, and the head 600 is attached to the fourth front rolling contact surface 440 of the fourth segment 400. In FIG. 8, the wire and the head are omitted.

The rear end of the wires 610, 620 passes through the articulating structure 10 and extends to the rear end of the tube 11 through the tube 11 (see FIG. 1). A wire driving means not shown is installed at the rear end of the tube 11, and the wires 610, 620 are connected to the wire driving means. The wire driving means works to pull or release each of the wires 610, 620 in the lengthwise direction Z of the articulating structure 10.

The wires 610, 620 are made of a material having some elasticity, and in the initial state, the wire driving means pulls the two wires 610, 620 with equal tension. Accordingly, a force is applied to the articulating structure 10 rearwards symmetrically in the second direction Y. The articulating structure 10 may be fixed to the initial state by the balanced tension of the two wires 610, 620.

Because the space of the coupling element is larger than the projection, when the projection is inserted into the coupling element during assembly of the articulating structure 10, as shown in FIG. 4, in the two segments, the projection may not be placed in a right position located at the center of the coupling element and may be positioned close to one side of the coupling element (i.e., there is a likelihood that the two segments may be placed in a misaligned position relative to each other). In this case, the two segments may not come into line contact along the set contact line 21 or 22.

According to this embodiment, as the wires 610, 620 are tightly pulled back with equal tension, a force is applied such that the wire connection holes are substantially arranged in a straight line along the lengthwise direction Z of the articulating structure 10, and in this process, the two misaligned segments may be corrected into a right position.

To steer the articulating structure 10, for example, the wire driving means may increase the tension by pulling the second wire 620, and on the contrary, release the tension applied to the first wire 610.

Accordingly, the right direction of the second direction Y of the fourth segment 400 is pulled back by the head 600, and the head 600 pushes back the first to fifth segments 100 to 500.

In this instance, even though the head 600 pushes back the first to fifth segments 100 to 500, the second segment 200 and the third segment 300, and the first segment 100 and the fifth segment 500 in line contact along the second contact line 22 cannot make relative movements with respect to each other. In contrast, as shown in FIG. 8, the first segment 100 and the second segment 200, and the third segment 300 and the fourth segment 400 in line contact along the first contact line 21 are slanted rightward of the second direction Y. In detail, the second segment 200 and the third segment 300 are slanted with respect to the first segment 100, and the fourth segment 400 is further slanted with respect to the slanted third segment 300. That is, bending occurs at two connection joints between the first segment 100 and the second segment 200 and between the third segment 300 and the fourth segment 400, and the tip of the articulating structure 10 is steered in the second direction Y.

As described above, the tool connection hole is formed at the center of each segment, and a tool connection passage 680 through which the tool passes is formed by the tool connection holes. Various types of surgical instruments, for example, an endoscope camera, a lighting device and a surgical instrument, inserted from the rear end of the tube 11 may be exposed through the front surface of the distal segment 400 through the tool connection passage 680.

As described above, as the tip of the articulating structure 10 is steered in the second direction Y, the surgical instrument may be steered in the second direction Y.

When the wire driving means increases the tension by pulling the first wire 610 while releasing the tension applied to the second wire 620, the first contact line 21 of the first segment 100 and the second segment 200, and the third segment 300 and the fourth segment 400 moves to the center as in the initial state, and the articulating structure 10 steered rightward of the second direction Y may return to the initial state. Further, when the wire driving means keeps pulling the first wire 610 while releasing the tension applied to the second wire 620, the articulating structure 10 may be steered leftward of the second direction Y that is opposite to FIG. 8.

Figure 9:
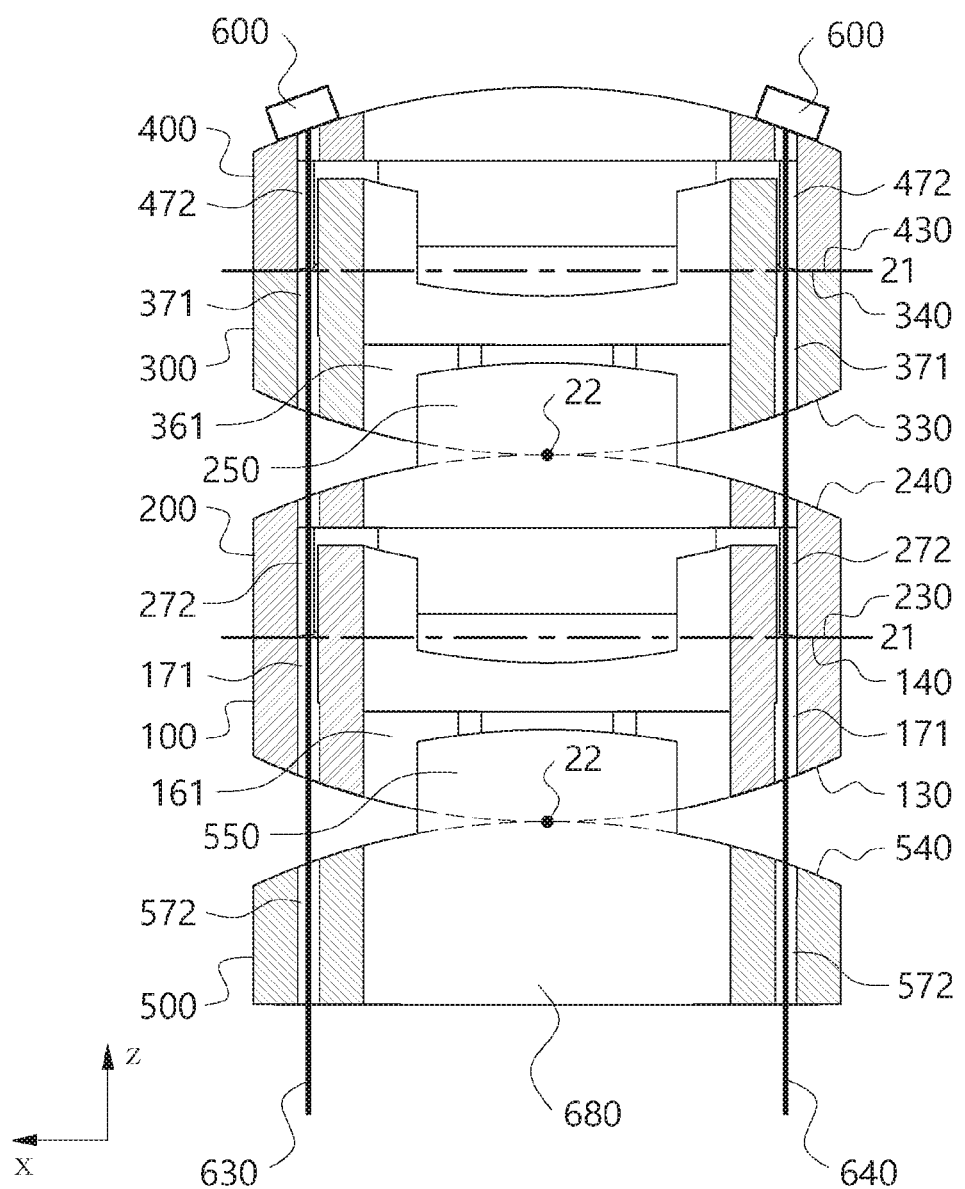
FIG. 9 is a cross-sectional view of an articulating structure when viewed from a second direction.
Figure 10:
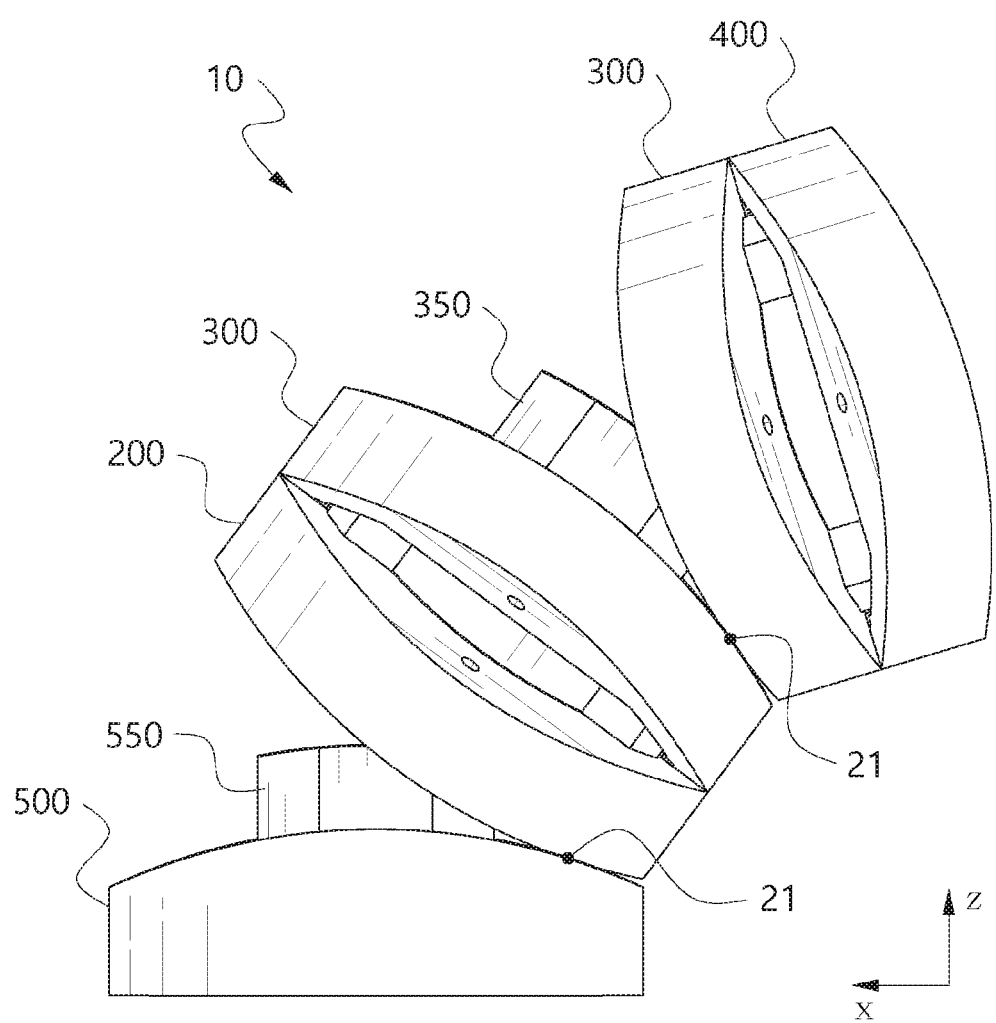
FIG. 10 is an operational state diagram of an articulating structure when viewed from a second direction.

FIG. 9 is a cross-sectional view of the articulating structure 10 when viewed in the second direction Y, and FIG. 10 is an operational state diagram of the articulating structure 10 when viewed in the second direction Y.

As shown in FIG. 9, in the initial state in which the articulating structure 10 is placed in a straight line, the first wire connection holes 171, 272, 371, 472, 572 formed in each segment 100 to 500 are also aligned in the lengthwise direction Z of the articulating structure 10, forming a substantially linear wire connection passage.

Each wire 630, 640 passes through the two first wire connection holes 171, 272, 371, 472, 572 arranged in the first direction X.

As shown in FIG. 9, for example, the front end of the wires 630, 640 is connected to the head 600 having a larger diameter than the first wire connection hole, and the head 600 is attached to the fourth front rolling contact surface 440 of the fourth segment 400. In FIG. 10, the wire and the head are omitted.

Likewise, the rear end of the wires 630, 640 passes through the articulating structure 10 and extends to the rear end of the tube 11 through the tube 11 (see FIG. 1), and is connected to the wire driving means.

In the initial state, the wire driving means pulls the two wires 630, 640 with equal tension. Accordingly, a force is applied to the articulating structure 10 rearwards symmetrically in the first direction X. The articulating structure 10 may be fixed to the initial state by the balanced tension of the wires 630, 640.

To steer the articulating structure 10, for example, the wire driving means may increase the tension by pulling the fourth wire 640, and on the contrary, release the tension applied to the third wire 630.

Accordingly, the right direction of the first direction X of the fourth segment 400 is pulled back by the head 600, and the head 600 pushes back the first to fifth segments 100 to 500.

In this instance, even though the head 600 pushes back the first to fifth segments 100 to 500, the first segment 100 and the second segment 200, and the third segment 300 and the fourth segment 400 in line contact along the first contact line 21 cannot make relative movements with respect to each other. In contrast, as shown in FIG. 10, the second segment 200 and the third segment 300, and the first segment 100 and the fifth segment 500 in line contact along the second contact line 22 are slanted rightward of the first direction X. In detail, the first segment 100 and the second segment 200 are slanted with respect to the fifth segment 500, and the third segment 300 and the fourth segment 400 are further slanted with respect to the slanted second segment 200. That is, bending occurs at two connection joints between the second segment 200 and the third segment 300 and between the first segment 100 and the fifth segment 500, and the tip of the articulating structure 10 is steered in the first direction X. Accordingly, the surgical instrument exposed to the front side of the articulating structure 10 through the tool connection passage 570 may be steered in the first direction X.

When the wire driving means increases the tension by pulling the third wire 630 while releasing the tension applied to the fourth wire 640, the second contact line 22, namely, a connection line of the second segment 200 and the third segment 300, and the first segment 100 and the fifth segment 500 moves to the center as in the initial state, and the articulating structure 10 steered rightward of the first direction X may return to the initial state. Further, when the wire driving means keeps pulling the third wire 630 while releasing the tension applied to the fourth wire 640, the articulating structure 10 may be steered leftward of the first direction X that is opposite to FIG. 10.

Although the steering of the articulating structure 10 in the first direction X and the second direction Y is separately described in FIGS. 7 to 10, it will be understood that it is possible to steer the articulating structure 10 in the first direction X and the second direction Y at the same time when the wire driving means manipulates the first to fourth wires 610 to 640 at the same time. That is, it is possible to steer the tip of the articulating structure 10 3-dimensionally within the bending limit of the articulating structure 10.

In this instance, the articulating structure 10 is independently steered in the first direction X and the second direction Y by the pair of wires arranged in the first direction X and the pair of wires arranged in the second direction Y respectively, thereby simplifying the computation for 3-dimensional composite direction control of the tip.

According to this embodiment, in one segment, the front rolling contact surface and the rear rolling contact surface are arranged by 90°, and the arrangement direction of the projections formed on the front rolling contact surface and the arrangement direction of the coupling elements formed on the rear rolling contact surface is arranged by 90°, to provide 2 degree of freedom to the articulating structure 10, but the present disclosure is not limited thereto. For example, in the first segment 100, both the first front rolling contact surface 140 and the first rear rolling contact surface 130 are formed as part of the circumference of a circular cylinder around an imaginary axis line of the first direction X, and the two coupling elements 161 formed on the first rear rolling contact surface 130 may be arranged in the first direction X. When segments of the same configuration as the first segment 100 formed as described above are connected in series one after another on the front and rear sides of the first segment 100, the articulating structure 10 may be a structure of 1 degree of freedom that bends in only the second direction Y. In this case, four wires are not necessary, and only the first wire 610 and the second wire 620 and their connection holes may be formed.

As described above, the coupling element 161 and the projection 150 may be arranged by 90° or in the same direction since the projection protrudes forward from the front rolling contact surface, and on the contrary, the coupling element is recessed in the rear rolling contact surface opposite the front rolling contact surface. That is, it is possible to change the arrangement position of the projection and the coupling element without reducing the height or radius of the segment.

According to this embodiment, the projection may be inserted into the coupling element simply by placing one segment in front of other segment without applying a force when inserting the projection into the coupling element, and thus the assembly performance of the articulating structure 10 is very high.

Additionally, in this embodiment, while the projection increases the side stiffness for a direction perpendicular to the rolling movement direction, it is possible to achieve relative segment steering by the rolling movements by the rolling contact surface without using the projection as a hinge for the pivot of two segments, thereby maintaining the smooth steering advantage by rolling movements.

Although this embodiment designates a fifth segment, a first segment, a second segment, a third segment and a fourth segment in the order of from proximal to distal of the articulating structure 10, it should be understood that the segment name is not intended to limit the designation of the first to third segments described in the appended claims.

For example, the segment 500, the segment 100 and the segment 200 arranged one after another from proximal may be a first segment, a second segment and a third segment respectively, and on the contrary, the segment 400, the segment 300 and the segment 200 arranged one after another from distal may be a first segment, a second segment and a third segment respectively. Additionally, for example, the segment 200, the segment 300 and the segment 400 may be a first segment, a second segment and a third in the appended claims.

What is claimed is:

1. An articulating structure that bends by relative movement of a plurality of segments connected in series, the articulating structure comprising:
   a first segment and a second segment arranged in contact with each other,
   wherein the first segment has a first front rolling contact surface and a projection protruding forward from the first front rolling contact surface,
   the second segment has a second rear rolling contact surface and a coupling element recessed in the second rear rolling contact surface, and
   the projection is inserted into the coupling element,
   wherein the second rear rolling contact surface is in line contact, not in face contact, with the first front rolling contact surface on a first direction contact line extending in a first direction,
   the first segment and the second segment make a relative rolling movement during which the first direction contact line moves while maintaining the line contact, and
   the projection supports the first segment and the second segment for the first direction.

2. An articulating structure that bends by relative movement of a plurality of segments connected in series, the articulating structure comprising:
   a first segment and a second segment arranged in contact with each other,
   wherein the first segment has a first front rolling contact surface, and the second segment has a second rear rolling contact surface in contact with the first front rolling contact surface on a first direction contact line extending in a first direction,
   the first segment has a projection protruding forward from the first front rolling contact surface, and the second segment has a coupling element recessed in the second rear rolling contact surface, wherein the projection is inserted into the coupling element,
   the first segment and the second segment make a relative rolling movement for translation of the first direction contact line while maintaining the line contact, and
   the projection supports the first segment and the second segment for the first direction,
   wherein the projection is formed with such a length as to prevent a front end of the projection from coming into contact with a bottom surface of the coupling element while keeping at least part of the projection inserted into the coupling element during the rolling movement.

3. The articulating structure according to claim 1, wherein two projections are spaced in the first direction apart from a center of the first segment on the first front rolling contact surface.

4. The articulating structure according to claim 1, wherein the projection has a width of a second direction perpendicular to the first direction,
   the coupling element has a width of the second direction, and
   the width of the projection is smaller than the width of the coupling element.

5. An articulating structure that bends by relative movement of a plurality of segments connected in series, the articulating structure comprising:
   a first segment and a second segment arranged in contact with each other,
   wherein the first segment has a first front rolling contact surface, and the second segment has a second rear rolling contact surface in line contact with the first front rolling contact surface on a first direction contact line extending in a first direction,
   the first segment has a projection protruding forward from the first front rolling contact surface, and the second segment has a coupling element recessed in the second rear rolling contact surface, wherein the projection is inserted into the coupling element,
   the first segment and the second segment make a relative rolling movement for translation of the first direction contact line while maintaining the line contact, and
   the projection supports the first segment and the second segment for the first direction,
   wherein the plurality of segments has a wire connection hole passing through front and rear surfaces of each segment, and
   a wire passage groove through which a wire passes is formed on an outer surface of the projection.

6. The articulating structure according to claim 5, wherein when the articulating structure is placed in a straight line, a wire passes through the wire connection holes of each segment arranged such that the wire connection holes are aligned in a lengthwise direction of the articulating structure, and
   the plurality of segments makes the relative movement by pulling or releasing the wire in the lengthwise direction of the articulating structure.

7. The articulating structure according to claim 6, wherein the wire connection holes include a pair of first direction wire connection holes arranged in the first direction and a pair of second direction wire connection holes arranged in a second direction.

8. The articulating structure according to claim 1, wherein the first front rolling contact surface and the second rear rolling contact surface are formed as part of a circumference of a circular cylinder.

9. The articulating structure according to claim 1, wherein an outer surface and an inner surface of the projection are formed as a convex surface that curves outward in a radial direction of the first segment.

10. The articulating structure according to claim 1, further comprising: a third segment positioned in contact with the second segment,
    wherein the second segment has a second front rolling contact surface opposite the second rear rolling contact surface, and the third segment has a third rear rolling contact surface in line contact with the second front rolling contact surface, and
    the second segment has a projection protruding forward from the second front rolling contact surface, and the third segment has a coupling element recessed in the third rear rolling contact surface, wherein the projection of the second segment is inserted into the coupling element of the third segment.

11. The articulating structure according to claim 10, wherein the second front rolling contact surface and the third rear rolling contact surface are in line contact with each other on a second direction contact line extending in a second direction perpendicular to the first direction,
    the second segment and the third segment make a relative rolling movement during which the second direction contact line moves while maintaining the line contact of the second front rolling contact surface and the third rear rolling contact surface, and the projection of the second segment supports the second segment and the third segment for the second direction.

12. The articulating structure according to claim 1, wherein a tool connection hole passing through upper and lower surfaces of each segment is formed at a center of the plurality of segments.

13. A tube insert device, comprising:
an elongated tube; and
the articulating structure according to claim 1, connected to a front end of the tube.

* * * * *